US007338173B2

(12) United States Patent
Dick et al.

(10) Patent No.: US 7,338,173 B2
(45) Date of Patent: Mar. 4, 2008

(54) METHOD AND DEVICE FOR THE SUBJECTIVE DETERMINATION OF ABERRATIONS OF HIGHER ORDER

(75) Inventors: Manfred Dick, Gefell (DE); Eckhard Schroeder, Eckental (DE); Holger Maeusezahl, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 664 days.

(21) Appl. No.: 10/470,149

(22) PCT Filed: Jan. 28, 2002

(86) PCT No.: PCT/EP02/00871

§ 371 (c)(1),
(2), (4) Date: Jan. 12, 2004

(87) PCT Pub. No.: WO02/060319

PCT Pub. Date: Aug. 8, 2002

(65) Prior Publication Data

US 2005/0225750 A1    Oct. 13, 2005

(30) Foreign Application Priority Data

Jan. 27, 2001    (DE) ................ 101 03 763

(51) Int. Cl.
*A61B 3/00*    (2006.01)
(52) U.S. Cl. .................... 351/246; 351/205
(58) Field of Classification Search ........ 351/200, 351/205, 206, 211, 212, 215, 246, 247
See application file for complete search history.

(56) References Cited

U.S. PATENT DOCUMENTS 5,016,977 A    5/1991    Baude et al.
5,777,719 A    7/1998    Williams et al.
6,042,233 A    3/2000    Mihashi et al.
6,050,687 A    4/2000    Bille et al.
6,460,997 B1 *   10/2002    Frey et al. ............... 351/211

FOREIGN PATENT DOCUMENTS

WO    9927334    6/1999

OTHER PUBLICATIONS

Lopez-Gil et al., Generation of Third Order Spherical an Coma Aberrations by use of Radially Symmetrical Fourth Order Lenses, vol. 15, No. 9, Sep. 1998, J. Opt. Soc. Am. A.
Junzhong Liang et al., "Objective measurement of wave aberrations of the human eye with the use of a Hartmann-Shack wave-front sensor", Optical Society of America, Optics and Image Science, vol. 11, No. 7, pp. 1949-1957, 1994, Heidelberg, Germany.
David Williams' Lab, "Wavefront sensing and the eye's optical quality", Center for Visual Science, University of Rochester, pp. 1 - 4, Internet: www.cvs.rochester.edu/williamslab/research/option01.html.

* cited by examiner

*Primary Examiner*—Hung Xuan Dang
(74) *Attorney, Agent, or Firm*—Darby & Darby

(57) ABSTRACT

A device for the subjective determination of aberrations of higher orders Xi in an optical system, in particular in an eye includes at least one observation channel into which defined plates can be introduced, the individual plates having optically active structures which correspond to a defined Zernike polynomial and to a defined amplitude, at least one order Xi of the Zernike polynomial being greater than two.

4 Claims, 3 Drawing Sheets

10    5    2.5    1.0    0.5

Subset A 10    5    2.5    1.0    0.5

Subset B

METHOD AND DEVICE FOR THE SUBJECTIVE DETERMINATION OF ABERRATIONS OF HIGHER ORDER

BACKGROUND

The present invention relates to a method and a device for the subjective determination of aberrations of higher order in an optical system, in particular in an eye.

In order to improve the quality of optical systems such as imaging systems and laser irradiation, optical wavefronts of these systems are analysed. In the article "Objective measurement of wave alternations of the human eye with the use of a Hartmann-Shack wave front sensor" by Liang et al, Optical Society of America 1994, p. 1949 ff., it is described how, with Shack-Hartmann sensors, aberrations of higher order can be recorded and evaluated in the form of Zernike coefficients of the various orders.

This objective determination of the Zernike coefficients results in an improvement in quality of the system. However, this objective improvement in quality displays differences from the subjectively evaluated visual power of this optical system.

This fact has been taken into account for the conventional spherocylindrical correction of refractive errors of the human eye in that the ophthalmologist objectively establishes the correction values by means of refractometers and then, in order to provide the subjective fine adjustment for the patient, determines the final data by means of test spectacles or a phoropter and a reading chart. For higher aberrations (starting from the $3^{rd}$ order), these subjective tests end merely in a straight decision that the correction does or does not achieve certain effects. However, a subjective fine adjustment is not possible.

Beyond the normal spherical and cylindrical correction of aberrations, in order to correct higher aberrations as well, adaptive lenses can be used in theory which operate as deformable mirrors in reflection or liquid crystal lenses in transmission. Despite intense efforts, however, these adaptive lenses cannot yet be used industrially due to their sensitivity.

SUMMARY OF THE INVENTION

An object of the present invention is to provide a method and a device for the subjective determination of aberrations of higher orders in an optical system, with which a subjective fine adjustment is easily possible.

The present invention provides a device for a subjective determination of aberrations of higher orders in an optical system. The device includes an observation channel and a plurality of individual plates configured to be introduced into the observation channel. Each plate has optically active structures corresponding to a defined Zernike polynomial and to a defined amplitude of the defined Zernike polynomial. The defined Zernike has an order greater than two.

In particular, the present invention provides a device for the subjective determination of aberrations of higher order Xi in an optical system, in particular in an eye, comprising at least one observation channel into which defined plates can be introduced, the individual plates having optically active structures which correspond to a defined Zernike polynomial and a defined amplitude, at least one Zernike polynomial having an order greater than two.

Such an optical system can be for example an eye, in particular a human eye. The optical system can also be an optical instrument for examining the ocular fundus (retina) in which the aberration of higher order of the specially examined eye is compensated. Furthermore, it is possible to understand as an optical system optical instruments such as telescopic sights or eyepieces of the microscope together with the eye looking through these. In addition, an optical system can be a beam-guiding system such as a laser or laser diodes in which aberrations of higher orders are to be corrected.

The observation channel is a defined path in which correction elements, in particular plates, can be introduced. This observation channel can be a free space, a vacuum or also a (partially) transmitting medium, such as air, gas or liquid. The observation channel is particularly preferably a tube which protects the area surrounding it from external influences such as atmospheric fluctuations, dust, etc.

Aberrations of higher orders Xi in an optical system are aberrations which occur as wavefront aberrations and can thus be formulated mathematically in the most varied manner. The aberrations are particularly preferably described here by Zernike polynomials. The advantage of this description is firstly the orthogonality and secondly each polynomial stands for a known aberration in the lens (astigmatism, coma, etc.). The wavefront aberration $W(p,\theta)$ is therefore described by the overlaying of the individual polynomials $Z_n(p,\theta)$.

$$W(p, \theta) = \sum_{k=0}^{n} k_n Z_n(p, \theta)$$

This property is exploited in the present invention by using a phase-plate set for each term $k_n Z_n(p,\theta)$ of the sum.

Starting from these properties of the Zernike polynomials, the orthogonality and the description of an optical image error, in the present invention the aberrations are preferably determined and corrected independently of each other. To this end, in each case a set of phase plates $P^m$ is preferably used, which correspond to a Zernike polynomial $W_z(p,\theta)$ and are classified in terms of their coefficient $k_z$ (the amplitude of the wavefront portion). The classification is carried out such that each amplitude can be set quasi-continuously via combinations. For the present invention, such a set of phase plates is preferably used for each Zernike polynomial—and therefore for each imaging or image error.

In addition to image errors as parameters, a phase-plate set has the optical zone as a characterizing variable in which the wavefront correction is carried out. This can also be universally varied and set.

The individual plates have optically active structures which correspond to a defined Zernike polynomial and to a defined amplitude, i.e. to a defined polynomial coefficient $k_z$. Thus an optically active structure which precisely corrects this aberration can be applied to a plate for a special Zernike coefficient, i.e. for a special coefficient of a special Zernike polynomial. The optically active structure which is applied to the individual plates then also differs with regard to a specially defined Zernike polynomial from other plates with this optically active structure by different defined amplitudes or polynomial coefficients. For example, a set of plates which corrects the individual aberration to a varying intensity results from a sensibly selected series of different amplitude strengths for the same Zernike polynomial.

Particularly preferably, several aberrations of various terms of Zernike polynomials can also be combined on one plate. Thus it is conceivable to combine all $4^{th}$-order errors in one plate or else to realize individual terms of the Zernike polynomials with different coefficients on one plate (for example an X1 coefficient k1 with term X2 and coefficient k2=2×k1).

As a result of this, a device is provided in which an aberration of higher order in the corresponding optical system can be corrected by simple introduction of a correspondingly defined plate. By combining several plates which are introduced one behind the other into the observation channel, the sum of the aberrations of the errors corrected by the individual plates can be established or compensated by the addition of the Zernike polynomials.

In a preferred embodiment of the present invention, a device with a plate set of plates is provided which has optically active structures to compensate aberrations of at least one defined Zernike polynomial. As a result of this, it is possible to provide a plate set for a special aberration, corresponding to a Zernike polynomial, in which each plate of this set corrects a special aberration. Thus, for example a set can comprise plates to compensate aberrations of a third-order Zernike polynomial and to compensate aberrations of a fourth-order Zernike polynomial. It is also possible for aberrations of Zernike polynomials of lower order, for example second order, to be corrected by further plates. By adding different plates, a more complex aberration, or the whole wavefront, can then be calculated or compensated.

In a further embodiment of the present invention, a device is provided in which a plate set has a subset of plates which has individual plates with optically active structures to compensate aberrations of various amplitudes for a defined Zernike polynomial. As a result it is possible, in the case of an aberration which corresponds to a Zernike polynomial, to provide a subset of different plates which also compensate the aberration of this Zernike polynomial, but with different amplitudes or coefficients. With the help of such a subset of plates, it is possible to delimit and particularly finely adjust the aberration with regard to the Xn polynomial by optional, iterative or alternating use of the different plates of the subset. Particularly preferably, the individual plates of a subset are sorted and combined in a classified manner, so that the individual plates are arranged according to their amplitudes. The aberration can thus be delimited very accurately both by selecting one of the plates of the subset and combining different plates of the same subset. In addition, it is possible to correct the entire aberration of different higher orders Xi in the optical system by adding different plates from different subsets.

A plate set and/or a subset of plates is particularly preferably arranged on a circular disc. This circular disc is particularly preferably located in a device which is developed as a phoropter. As a result, it is possible to resort to proven mechanical structures in order to determine and to compensate errors of the third and higher order in a novel way.

In a particularly preferred version of the present invention, a target apparatus for the patient's view is additionally provided. In this way, it is possible to satisfy strict requirements in respect of the alignment of the individual plates relative to the optical axis, for example of the eye which looks through. The inlet and outlet aperture of the phase-plate phoropter can be used as a target apparatus. This can be centred for example so that the visual axis of the eye coincides with the optical axis of the phase-plate phoropter.

The plates are particularly preferably made of glass or plastic. They preferably consist of a transmitting plastic. The plates are preferably made by means of spot-scanning excimer lasers by ablation of thin plastic or special-glass plates. The plates are particularly preferably made of PMMA. Other transparent materials that are easily processable by means of lasers are also particularly preferably used. The processing laser advantageously has a Gaussian beam profile. Furthermore, processing machines of the optical industry that are directed to precise points can be used to produce the thin glass plates with a high-precision surface polishing quality, for example by "single point diamond turning technology". Crystals are also preferably used here.

The device according to the invention is particularly preferably used for the subjectively evaluated establishment of the aberration of higher order within the framework of the determination of visual acuity. This is a sight test which precedes for example a correction using reading aids or a laser. In this way, the aberrations detected for example by objective wavefront aberration can again be subjectively finely adjusted and can thus be used to increase the quality of the objectively established theoretical output data.

The device according to the invention is also preferably used to optimize the resolution of optical instruments, such as for example during examinations of the ocular fundus (retina) by compensating the aberrations of higher order of the special eye. During this observation of the rear section of the eye for medical purposes, the aberration of the eye to be examined plays a not insignificant role in this high-precision and high-resolution observation, as it limits the resolution of the area to be examined. In order to compensate the aberration of this eye for observations with a fundus camera or similar, the device according to the invention can be used and a set of phase platelets that fully compensate the aberration can be introduced into the beam path. The best possible observation and resolution and optimum optical quality is therefore possible. It is particularly advantageous in the case of this use that the aberrations can be rapidly compensated universally for different eyes by preferably setting the phoropter phase plates to a known value.

The device according to the invention is particularly preferably used to correct beam profiles of beam sources, in particular of laser diodes. The forming of wavefronts which emerge from beam sources is a task which is often set. There are above all two requirements here. Firstly, the provision of ideal wavefront profiles (flat wave/pure Gauss profile) and secondly the intentional deformation or intentional forming of wavefront profiles. The use of the present invention in laser diodes is to be named here as an example. For a broad application, the correction or fine correction of the established wavefront profile is necessary. To this end, the wavefront aberration is conventionally recorded and corrected by means of phase plates of the present invention. As a result, it is possible to create one and the same wavefront profile with each laser diode which can vary substantially in its wavefront aberrations. This is easily and universally possible by means of the present invention. This approach therefore differs greatly from the production of a correction plate for a particular laser diode for a particular optical application. In the absence of the laser diode, the correction plate can no longer be used and a new correction plate must be produced for the new laser source. This can be universally solved when using the present invention as the new radiation source can then also be individually corrected with the device according to the invention.

A further advantageous use of the device according to the invention relates to the individual correction of vision defects, in particular when using optical instruments. When using optical instruments, an increase in quality can result from the correction of aberrations of higher order, in particular those caused by vision defects, by using the device according to the invention. This can be used for example in the hunter's telescopic sight or in the eyepiece of the microscope. It is possible here to obtain optimum resolution by individual subjective determination of the aberrations. Not only a defect-free, but even a superproportional visual acuity which goes beyond full visual power can be achieved here.

The object of the present invention is also achieved in particular by a method for the subjective determination of an aberration of a special higher order x in an optical system, in particular an eye, in which in a first step a plate is introduced into an observation channel of the optical system, the plate having optically active structures which correspond to a defined Zernike polynomial and to a defined amplitude, the order x of the Zernike polynomial being greater than 2, in a second step a subjective assessment of the current wave deformation of the defined order x is carried out and in a third step comprising the repeated application of the first step with plates of different amplitude correction of the same defined Zernike polynomial and of the second step of the subjective determination, the plate and therefore the amplitude correction is established which subjectively best compensates this aberration of the special higher order x. This method can be used iteratively or alternately and thus leads to a minimum of deviation. Due to this universal possibility of analyzing wavefront profiles, these can be compensated on the basis of a target value. The wavefront profile can be iteratively established by the modular principle and guided to a minimum of deviation.

In a particularly preferred method of the present invention, the previously described method is carried out successively for each of the occurring aberrations of different orders X1-Xn. The addition of the corrections for the individual polynomial coefficients produces the total correction of the aberrations of the optical system.

BRIEF DESCRIPTION OF THE DRAWINGS

The present invention will be explained further in the following with reference to the drawings, in which.

DETAILED DESCRIPTION

Figure 1:
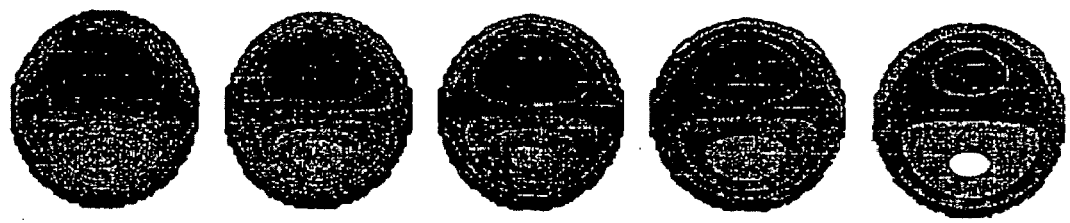
FIG. 1: a plate set for the $3^{rd}$-degree coma image errors in the x axis and $3^{rd}$-order spherical aberration, each with a subset for polynomial coefficients from 0.5 to 10.
Figure 1:
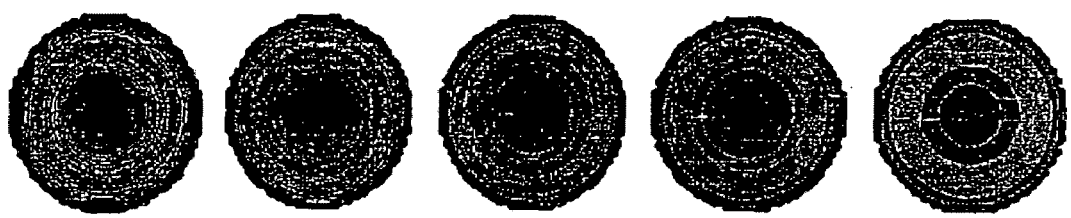

A plate set for $3^{rd}$-degree coma image errors of the x axis and $3^{rd}$-order spherical aberration, each with a subset for polynomial coefficients from 0.5 to 10, is schematically represented in FIG. 1. The plate set for $3^{rd}$-degree coma image errors in the x axis according to the formula $W(p,\theta)=(3p^2-2p)\sin(\theta)$ is designated A and the sub-plate set for the image error of the $3^{rd}$-order spherical aberration according to the formula $W(p,\theta)=6p^4-6p^2+1$ is designated B. These two subsets A and B together form the plate set according to FIG. 1. Subsets A and B each consist of five individual plates which are laid out within the defined Zernike polynomial for different polynomial coefficients, i.e. amplitudes. Thus subset A has individual plates for polynomial coefficients 0.5, 1.0, 2.5, 5 and 10. Subset B also consists of five plates with different polynomial coefficients 0.5, 1.0, 2.5, 5 and 10. With this plate set, consisting of subsets A and B, image errors can then be determined and compensated according to the two addressed Zernike polynomials. These aberrations of higher orders in these optical systems can be established and compensated in a targeted manner with the help of this ordered selection of phase plates by establishing in a targeted manner wavefronts which are deformed as desired and of which the spherical and cylindrical parts have previously been corrected with standard lenses, and by correcting the individual orders quasi-continuously and orthogonally. This takes place through a kind of modular principle with which a universal establishment and correction of any wave profiles can be carried out. Image errors of optical systems can thus be minimized and therefore maximum imaging quality can be achieved. In this way, a universal possibility is provided to analyze wavefront profiles and to compensate them on the basis of a target value. Through the modular principle, the wavefront profile is iteratively established and guided to a minimum of deviation. The plate set ideally consists of further subsets C, D . . . (not represented) in order to be able to compensate the desired image errors according to further Zernike polynomials.

Figure 2:
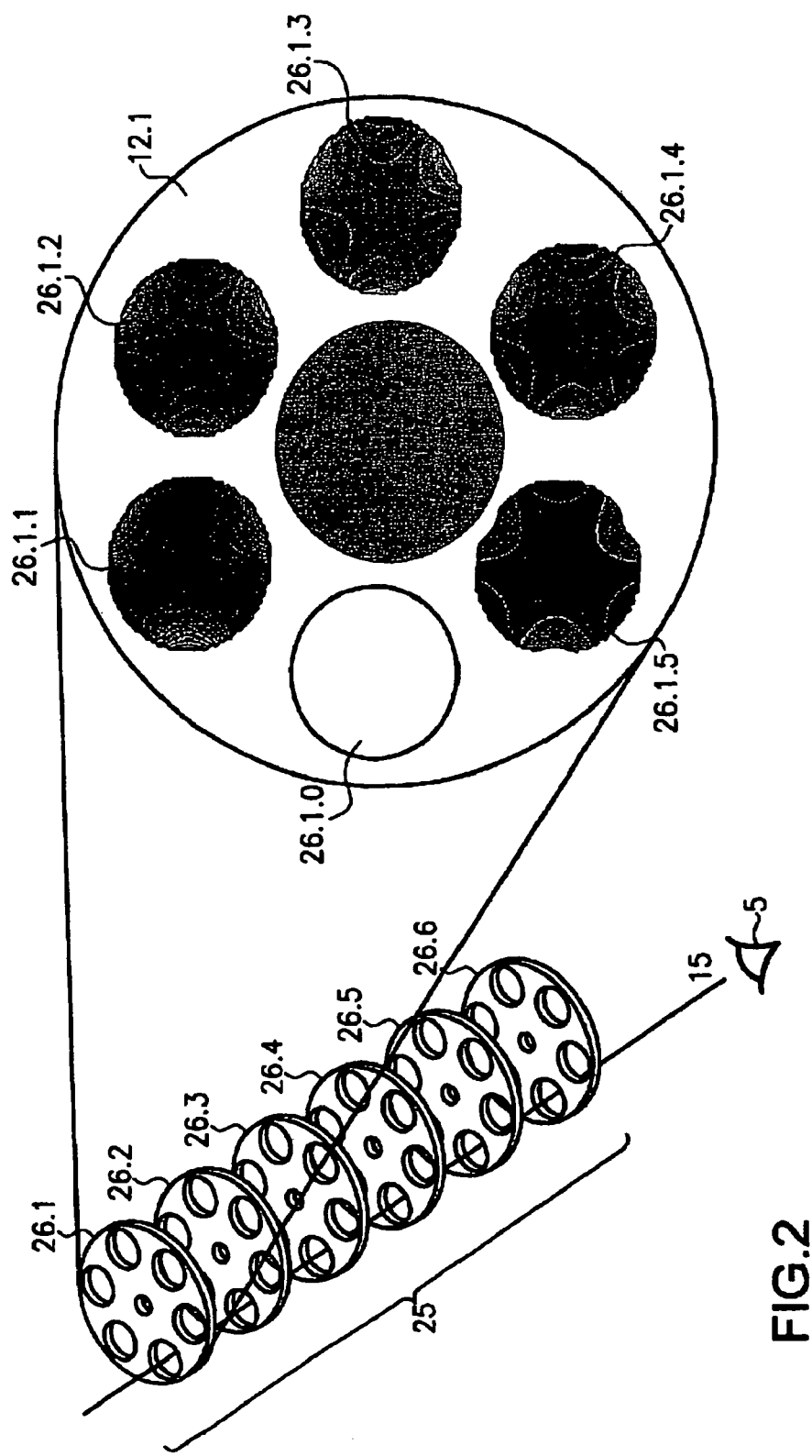
FIG. 2: an arrangement of circular discs with subsets of plates according to the present invention, each arranged in a circular disc.

An arrangement of circular discs with subsets of plates according to the present invention arranged, each in a circular disc, is schematically represented in FIG. 2. A plate set 25 is represented here with individual subsets 26.1 to 26.6 of a plate set, wherein, within the individual subsets 26 for one special Zernike polynomial in each case, plates of different amplitudes of this Zernike polynomial are provided in a classified manner, each in a circular disc. The circular disc 12.1 is represented particularly enlarged, on which plates 26.1.1 to 26.1.5 are represented which compensate the aberration of different amplitudes of a particular Zernike polynomial. In addition to these, an opening 26.1.0 has been left free—this corresponds to the amplitude 0 for this Zernike polynomial, i.e. indeed no correction of the corresponding aberration in error-free optical systems. In addition, an observation channel 15 is schematically represented by a straight line. Through this observation channel 15, an eye 5 can see centrally through a recess in each circular disc. The sum of the plates, swivelled in the observation channel, of the subsets 26 arranged on the individual circular discs 12 then have an effect on the eye.

In order to then establish the aberrations, all the circular discs 26.1 to 26.6 are aligned such that the plate with amplitude 0 of all the circular discs comes to rest in the observation channel 15, i.e. in the end that no compensations take place. One circular disc after the other is then further swivelled such that the person looking through the observation channel 15 can subjectively determine whether there is an improvement due to the individual plates of the subset and when this is at its most optimal. Once the optimum compensation of the individual plate of a subset is found, the next circular disc is swivelled or introduced into the observation channel 15 and thus the plates of the next subset are offered, until the optimum is also calculated for this aberration. After all six subsets are set via the circular discs such that in each case the plate with the optimal compensation is swivelled in the observation channel 15, the sum of the individual plates, which compensates the entire wavefront deformation optimally according to the person's subjective impression, has an effect on the eye 5.

With these transparent thin-glass or plastic plates and the thus-ordered number of phase plates in a circular disc which are classified in terms of their classification according to the order of the Zernike coefficients and the respective amplitude, these plates are incorporated in a defined manner into the mechanical system for example of a phoropter in which plates of an order of the Zernike coefficients with a different amplitude have preferably been arranged in a circular disc. Through centred arrangement of such circular discs one behind the other, it is possible to swivel optionally phase plates of a different order of the Zernike coefficients and of a different amplitude into an optical axis with a target apparatus. Thus, on this optical axis with target or centering apparatuses, every combination of aberrations of higher order can be corrected quasi-continuously for the eye or optical system to be corrected.

A particular advantage of this version lies in the comparatively robust reproducible design in which the lateral spatial resolution of the phase plates is determined by the production technology and can be in the submillimetre range. The additive structure of the Zernike polynomials allows an additive compensation of any wavefront deformation through to an ideal, desired wavefront (flat wave, etc.). A proven mechanical system is resorted to by the use of the phoropter principle for phase plates of a different strength of the respective aberration of higher order. Such a phase-plate phoropter particularly preferably has exactly centred phase plates which have with regard to position and angle deviation of less than 0.1 mm, or 0.1 degrees (dx, dy<0.1 mm; dv<0.1°), as well as particularly preferably a target apparatus for the patient's view. As a result of this, a subjective establishment of the value of the aberration of higher orders is possible within the framework of a sight test (determination of visual acuity) before a correction using vision aids or lasers. Furthermore, it is possible to optimize the resolution of optical moments when examining the ocular fundus (retina) by compensating the aberrations of higher order of the special eye. Furthermore, the aberrations of higher orders of any optical systems can be established and compensated with the help of a device according to the invention.

The procedure for the determination of an aberration of the human eye using the present invention is typically as follows: a phase platelet $P_n^m$ of a phase set $P^m$ is swivelled in front of the optical system of the eye. The eye and the optical axis of the phase platelets are overlaid by an optical target and centering apparatus. It is therefore guaranteed that the optical centres of the eye and of the phase platelets lie on top of each other. Thereafter the amplitude of this phase set is increased (by swivelling the next platelet $P_{+1}^m$ of the phase set $P^m$). This takes place iteratively, or alternately until the patient's subjectively firm image impression is found. Once this has taken place, the image error of the phase plate $P^m$ is described and guided to a subjective minimum.

In the next step, the above-described procedure is continued with the following set $P^{m+1}$ of phase plates which describe a further image error to be corrected. All previously found phase platelets $$P_{1\ldots n}^{1\ldots m}$$

of the optimal correction remain swivelled. Through this procedure, the patient is led step-by-step to an optimum—i.e. to the minimization of all the image errors.

The classification of the phase platelets is such that all the possible amplitudes can be set in a sensible range. The statistical occurrence of the aberrations in the optical systems or patients is used here a starting point. Particularly preferably, these curves are developed equidistant between a maximum and minimum value.

The lower limit of the wavefront amplitude is determined by the Rayleigh criterion from which it can be deduced that only wavefront differences of greater than $\lambda/4$ have a significant effect on the image quality. As a result, it is possible to determine subjectively the aberration of the eye in the case of wavefront deformations of higher orders, the natural light spectrum being able to be used simultaneously. This is not possible in the case of the known aberrometers for the determination of the wavefront deformation of higher order, as these require monochromatic light.

Figure 3:
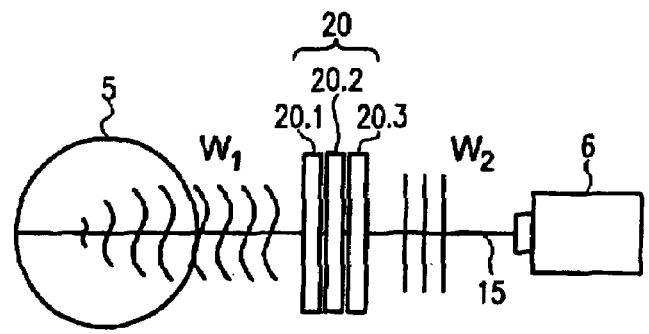
FIG. 3: an arrangement of a device according to the invention during the examination of an eye by means of a fundus camera.

A further advantageous application of the present invention will be explained with reference to FIG. 3. An arrangement of a device according to the invention for the examination of an eye by means of a fundus camera is schematically represented in FIG. 3. A camera 6 or a microscope or a slit lamp is represented here which can observe an eye 5 via an observation channel 15 (represented as an idealized optical axis in the form of a straight line). Phase plates 20.1 to 20.3 are introduced in the observation channel 15 between the eye 5 and the camera 6. The wavefront W1, which emerges from the eye 5, is deformed by aberrations due to the suboptimal optical system of the eye. This is symbolized by a corresponding wave-shaped representation of the wavefront W1. Upon passing through the phase plates 20.1 to 20.3, these errors of higher order are compensated so that the emerging wavefront W2 no longer has these aberration errors and therefore these deformations, and strikes the camera 6 as a flat wave.

As a result of this, an application in ophthalmology is opened up by an embodiment of the present invention, in which the rear section of the eye is observed. This serves for medical observations. For this high-precision and high-resolution observation, the aberration of the eye to be examined plays a not insignificant role, as it limits the resolution of the area to be examined. In order to compensate the aberrations of this eye for observation with a fundus camera or similar, a set of phase platelets which fully compensate the aberration is introduced into the beam path. Thus the best possible observation and resolution is possible with optimum optical quality.

Figure 4:
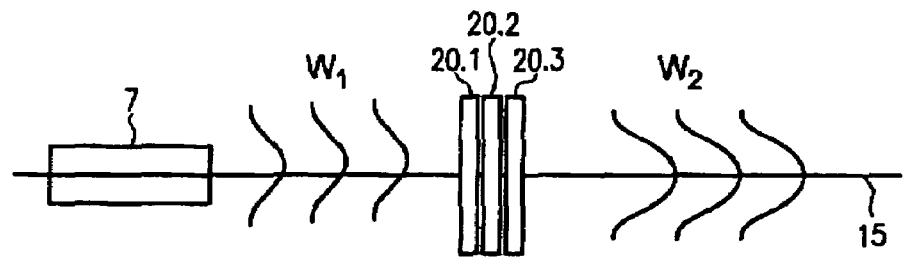
FIG. 4: a schematic representation of the use of the device according to the invention for the correction of the beam profile in laser diodes.

A further area of application is schematically represented in FIG. 4. The use of a device according to the invention for the correction of the beam profile in laser diodes is shown schematically here. A laser diode 7 serves as a beam source and emits beams along an observation channel lying in the optical axis (schematically represented by a straight line 15). The beams emerging at the laser diode 7 are spherocylindrically corrected (not represented) and strike phase plates 20.1 to 20.3 as wavefront W 1 with aberrations of higher orders. Here the beam profile is corrected such that it emerges as corrected beam profile W2 and has a desired wavefront W2. The forming of this wavefront from beam sources can be desired as a flat wave or as a pure Gaussian profile. Intentional deformation is involved here, or intentional forming of wavefront profiles. This is very easily and universally possible using a device of the present invention. A very fine correction of the established wavefront profile can thus be carried out for corresponding applications.

The wavefront aberrations are conventionally recorded and corrected by means of phase plates of the present invention. It is therefore possible to produce one and the same wave profile for each laser diode which varies greatly in its wavefront aberrations. The present invention therefore also differs greatly from the production of a correction plate for a particular laser diode for a particular optical application. In the absence of the laser diode or if the optical application is changed, this integral correction plate must be completely replaced. When using the present invention, the correspondingly corrected beam profile can be subsequently corrected or aligned for new applications. It is therefore possible to convert any forming of the wavefront profiles of beam sources by the universal use of the present invention.

Figure 5:
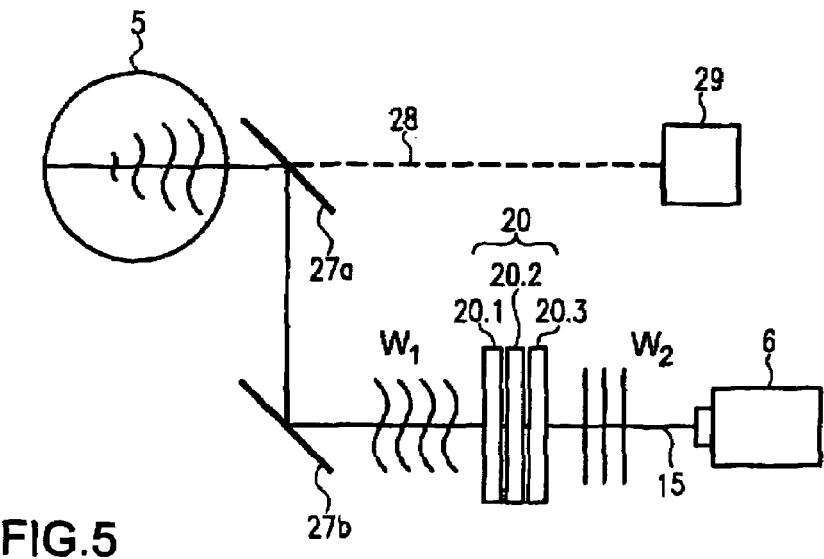
FIG. 5: an arrangement of a device according to the invention in a conjugated image plane.

The phase plates 20 can also be arranged in a conjugated image plane for example in the phase phoropter 2 according to FIG. 5. The observation channel 15 is arranged offset relative to the eye 5, for example roughly opposite the not directly examined eye. The beam path of the observation channel 15 is reflected into the eye 5 via an optical-square arrangement consisting of a first mirror 27a and a second mirror 27b, this can also be for example a prism arrangement or the like. The first mirror 27a can be designed semipermeable, so that a further device 29 can be arranged in the beam path 28 of the eye 5. This can be for example a device for the targeted stimulation of the eye 5.

With the present invention, a method of a device for the subjective determination of aberrations of higher order is provided, with which it is possible to compensate in a target-oriented manner aberrations of higher order with the help of an ordered selection of phase plates. Any wavefronts, which were previously corrected conventionally by spherical and cylindrical lenses or else corrected with integrated compensation of aberrations of higher orders of the form of aspherical orders, arranged in a targeted manner according to the amplitudes in the individual orders, can therefore be corrected quasi-continuously. The use of sensitive adaptive lenses can be dispensed with and it is made possible to reproducibly and quasi-continuously establish and compensate optical aberrations of higher order, in particular in ophthalmology, with a comparatively robust instrument.

The invention claimed is:

1. A method for the subjective determination of an aberration of a special higher order X in an optical system, comprising:

in a first step, introducing a first plate into an observation channel of the optical system, the plate having optically active structures corresponding to a defined Zernike polynomial having an order X and to a defined amplitude of the defined Zernike polynomial, the order X being greater than 2;

in a second step, subjectively assessing a current wave deformation of the order X; and in a third step repeating the first step with a second plate of different amplitude correction of the defined Zernike polynomial and repeating the second step of the subjective determination so as to select one of the first and second plates that subjectively best compensates the aberration of the special higher order X.

2. The method as recited in claim 1, wherein the optical system includes an eye.

3. A method for the subjective determination of aberrations of special higher orders X1 to Xn in an optical system, comprising:

in a first step, introducing a first plate into an observation channel of the optical system, the plate having optically active structures corresponding to a defined Zernike polynomial having an order X1 and to a defined amplitude of the defined Zernike polynomial, the order X1 being greater than 2;

in a second step, subjectively assessing a current wave deformation of the order X1; and in a third step repeating the first step with a second plate of different amplitude correction of the defined Zernike polynomial arid repeating the second step of the subjective determination so as to select one of the first and second plates that subjectively best compensates the aberration of the special higher order X1 in a fourth step, successively repeating the first and second steps for each defined Zernike polynomial having an order Xn, wherein Xn is greater than X1.

4. The method as recited in claim 3, wherein the optical system includes an eye.

* * * * *